United States Patent
Weissman (10) Patent No.: US 6,323,188 B1
(45) Date of Patent: *Nov. 27, 2001

(54) TREATMENT AND PREVENTION OF CARDIOVASCULAR DISEASES, HEART ATTACK, AND STROKE, PRIMARY AND SUBSEQUENT, WITH HELP OF ASPIRIN AND CERTAIN VITAMINS

(76) Inventor: Donald L. Weissman, P.O. Box 15927, Beverly Hills, CA (US) 90209

( * ) Notice: Subject to any disclaimer, the term of this patent is extended or adjusted under 35 U.S.C. 154(b) by 0 days.

This patent is subject to a terminal disclaimer.

(21) Appl. No.: 09/393,751

(22) Filed: Sep. 10, 1999

Related U.S. Application Data (63) Continuation-in-part of application No. 09/108,765, filed on Jul. 1, 1998, now Pat. No. 6,121,249.

(51) Int. Cl.$^7$ ............................. A61K 31/70; A61K 31/60
(52) U.S. Cl. ................................. 514/52; 514/165
(58) Field of Search ....................... 514/52, 165

(56) References Cited

U.S. PATENT DOCUMENTS 6,121,249 * 9/2000 Weissman et al. .................... 514/52

* cited by examiner

Primary Examiner—Raymond Henley, III
(74) Attorney, Agent, or Firm—Pillsbury Winthrop LLP (57) ABSTRACT

Disclosed is the method of reducing the incidence and severity of stroke, primary heart attack, and any subsequent heart attack or stroke in humans by daily administration of an effective amount of a combination of acetylsalicylic acid (ASA), a cyanocobalamin compound (Vitamin B12), a folic acid compound, and a pyridoxine compound (Vitamin B6) in an easy to take daily administration pack.

12 Claims, 6 Drawing Sheets

FIG. 1

HEALTHY HEART CARDIOLIFE

Ingredients

| | |
|---|---|
| ASPIRIN | 81 mg. |
| FOLIC ACID | 600 mcg. |
| $B_6$ | 50 mg. |
| $B_{12}$ | 100 mcg. |

Dimensions: 3" × 3"

| HEALTHY HEART Ingredients ||
|---|---|
| ASPIRIN | 81 mg. |
| FOLIC ACID | 600 mcg. |
| $B_6$ | 50 mg. |
| $B_{12}$ | 100 mcg. |
| VITAMIN E | 400 i.u. |
| VITAMIN C | 500 mg. |
| NIACIN | 100 mg. |

( 81 mg. )   ASA ( )   B$_6$, B$_{12}$, Folic Acid ( )
( )   Vitamin E 400 i.u.
      Vitamin C 500 mg.
      Niacin     100 mg.

FIG. 4

(81 mg.) ASA

B₆, B₁₂, Folic Acid

FIG. 5

( 81 mg. ) ASA ( ) B₆, B₁₂, Folic Acid

FIG. 6

TREATMENT AND PREVENTION OF CARDIOVASCULAR DISEASES, HEART ATTACK, AND STROKE, PRIMARY AND SUBSEQUENT, WITH HELP OF ASPIRIN AND CERTAIN VITAMINS

CROSS-REFERENCES TO RELATED APPLICATIONS

This application is a Continuation-In-Part of application Ser. No. 09/108,765, filed on Jul. 1, 1998, now U.S. Pat. No. 6,121,249, and said Ser. No. 09/108,765 application is incorporated herein by reference.

BACKGROUND OF THE INVENTION

1. Field of the Invention

This invention relates to a combination of aspirin, certain B vitamins and folic acid to prevent and or decrease cardiovascular diseases, heart attack and stroke, to a stable daily administration pack for such combination to facilitate the patient's compliance with recommendation or instruction to take such combination, and to the method of treating and preventing cardiovascular diseases with the help of such combination.

Cardiovascular disease ranks as the leading cause of mortality and morbidity in the United States today. This year, it is estimated that 1.5 million people will have a heart attack and that one third of those will die as a result of CAD.

The American College of Cardiology recently identified other abnormalities as factors for which intervention is likely to lower stroke and heart disease risk. Elevated total blood cholesterol is frequently considered a risk factor for coronary artery disease (CAD), but it is important to note that in the Framingham study 80% of CAD patients had the same total cholesterol as those who did not develop CAD.

2. Definition of Certain Terms

Throughout the specification and associated claims, terms listed below shall be read as having the meaning here stated:

| | |
|---|---|
| CAD | Coronary artery disease |
| LDL | Low density lipoprotein |
| IDL | Intermediate density lipoprotein |
| MI | Myocardial infarction |
| PVD | Peripheral vascular disease |

3. State of the Prior Art

Heredity remains the number one risk factor in heart disease; 77% of people in the United States with heart disease have inherited metabolic traits contributing to their atherosclerosis. Lp (a) is a LDL with protein (a) attached, and elevated level of Lp (a) is an inherited trait present in approximately 33% of heart disease patients. Elevated levels of Lp (a) increase the risk of heart disease by 300%, yet Lp (a) is not detected in traditional lipid profile tests. A powerful predictor of heart attacks in young men and of vein graft blockage following bypass surgery, elevated levels of Lp (a) also increase the danger of other risk factors. High Lp (a) can be treated with niacin. Niacin (nicotinic acid) or niacinamide is a member of the Vitamin B-complex group (vitamin B3). Buoyant LDLs are the lighter, larger LDLs found primarily in LDL pattern A people. Dense LDLs are the heavier, smaller LDLs found primarily in LDL pattern B people. LDL density change is the strongest predictor of percent change in coronary artery stenosis.

There is substantial evidence that reduction in small LDL is more important than reduction in LDL-cholesterol in achieving improvements. Following treatment with niacin, small LDL subclass patterns significantly improve with a larger LDL diameter. This is also associated with improvement in other abnormalities such as elevated IDL, elevated LP (a) and enhanced postprandial lipemia.

The chief drawback of using niacin in the treatment of hyperlipidemia is facial and truncal flushing, which occurs in nearly all users shortly after ingestion of a tablet with as small a dosage as 75 mg of niacin. It appears that niacin induces flushing by increasing the formation and/or release of some prostaglandin, which in turn increases the production of cyclic amp. Aspirin is a prostaglandin inhibitor and reduces the incidence and severity of flushing. Aspirin therapy has been well established as a platelet aggregate inhibitor and is now widely used. It has been shown to be the strongest therapeutic known to reduce the risk of a stroke, a first heart attack in healthy individuals, and subsequent heart attacks or strokes.

Recent evidence suggests that elevated blood levels of homocystine, which is derived from the amino acid methionine, is linked to heart disease. Homocystine is a sulfur-containing amino acid formed during the metabolism of methionine.

Homocystine increases the formation of highly atherogenic oxycholesterols, increases lipid peroxidation, and increases the oxidation of LDL in vitro. These observations suggest a potential role for antioxidant therapy in ameliorating homocystine-dependent oxidative vascular injury.

Patients with mild hyperhomocystinemia have none of the clinical signs of severe hyperhomocystinemia and are typically asymptomatic until the third or fourth decade of life when premature CAD develops, as well as recurrent arterial and venous thrombosis. How the body metabolizes, or breaks down, homocystine can be determined genetically. People who inherit a defective gene for homocystine metabolism tend to have elevated homocystine blood levels—a trait found in 20–30% of patients with atherosclerosis.

Three B-vitamins, folate and vitamins B6 and B12, play essential roles as cofactors in homocystine metabolism. Elevated plasma homocystine (even when caused by genetic variants) can usually be normalized by moderate vitamin supplementation. Folic acid alone, folic acid combined with B12 and B6, and vitamins B6 and B12 have all been shown to reduce homocystine concentrations. Normalization of the plasma homocystine concentration usually occurs within four to six weeks after the initiation of therapy, but may occur in as little as two weeks. Interestingly, the reduction in mortality from cardiovascular causes since 1960 has been correlated with the increase in vitamin B6 supplementation in the food supply.

A retrospective analysis of dietary vitamin C and E intake was done in the CLAS trial (n=156) and indicated an association between supplementary vitamin E intake and angiographically demonstrated reduction in coronary artery lesion progression.

The Cambridge Heart Attack and Antioxidant Study studied 2002 CAD patients, randomized to 800 IU vitamin E per day or placebo for 1.5 years, and revealed a significant reduction in non-fatal MI in the vitamin E group.

In recent years, however, awareness has grown that any medication regimen is only as good as the patient's compliance with it, that is that prescribed medications are actually taken at the times and in the amounts prescribed. The problem, and some ingenious but labor intensive and costly attempts to solve it, is well summarized in an article "The Other Drug Problem: Forgetting to Take Them" by science writer Abigail Zuber (New York Times, Jun. 2, 1998), which is here incorporated by reference in its entirety and from which the following is excerpted. "Study after study over the last 20 years has shown that misuse of prescription drugs is a worldwide epidemic every bit as dangerous and costly as an actual medical illness. It was tagged 'America's other drug problem' in the early 1990's when researchers consistently found it responsible for 10 to 25 percent of hospital and nursing home admissions studied. In 1984, the National Pharmaceutical Council, an association of pharmaceutical companies, estimated that misuse of prescription drugs had caused 125,000 deaths a year from heart disease alone. In 1993 the same organization calculated that not taking medicines correctly was draining upwards of $100 billion a year from the nation's economy in direct and indirect costs.

And with increased cost consciousness has come a new appreciation of the problem of 'noncompliance,' as medicine has labeled the phenomenon of skipping some doses, doubling up on others, forgetting to refill at the end of the month or taking a few of a family member's antibiotics on the chance they will work better than the ones prescribed.

Interest has been sharpened by new studies clearly demonstrating that disorders like elevated blood cholesterol or asthma respond far better when patients take medications as prescribed. And the flip side of the equation has been vividly illustrated by the medications for tuberculosis and AIDS: they may actually damage a patient's health when taken improperly, by inducing drug-resistant disease that may be passed on to others and cannot be treated at all. In fact, improving medication-taking behavior may be one of the few arenas in health care today where widely disparate interest groups—including medical researchers, patient advocates, drug companies, public health authorities and H.M.O. executives—share a goal. The result: an outpouring of medical articles and studies on the subject and a cornucopia of new tactics, devices and programs all aiming to cajole patients to remember their pills.

People in general take about 75 percent of their medications as prescribed,' said Joyce Cramer, a medical researcher at Yale University and an authority on drug-taking behavior. But within that figure the range of misbehavior is wide. Nancy Houston Miller, a nurse who is the associate director of Stanford University's Cardiac Rehabilitation Program in Palo Alto, estimated that 10 to 20 percent of patients grossly flout medication regimens—never filling the prescriptions or taking only a few token pills. About 50 percent take doses more or less correctly. And an all-important 30 to 40 percent in the middle are 'partial compliers,' forgetful enough that the medication may have only a fraction of its desired effect or may actually be harming them, but well-intentioned and able to be trained to do better.

Patients with serious diseases who are veterans at taking medication, cardiac-transplant patients, for instance—are usually better pill takers than those with silent conditions like high blood pressure, Dr. Urquhart said. But in general, predicting what patient will display which pill-taking behavior often yields surprises. Income, education, sophistication and competence in other parts of life correlate only very poorly with pill-taking behavior, the experts agree. People who know the purpose of the medication and the way it is supposed to work often do better than others. But education has its definite limits in inducing good pill-taking behavior: doctors, for example, are notoriously poor at it. In one large study of heart-attack prevention in male doctors in the 1980's, a full 30 percent of doctors were disqualified because they proved unable to take a single pill reliably every day.

Thus, as valuable as educational brochures, package inserts and videotapes may be, they are often now supplemented with a range of new compliance tools.

Some tools are million-dollar, labor-intensive programs. At Stanford, for instance, Ms. Miller has shown that heart-attack patients assigned to a nurse who spends hours educating them about diet, smoking, exercise and drug treatment, and then makes follow-up phone calls at home, are far more likely to stay on their medications than those who receive standard medical care.

Similarly, in New York City, a program in which city health department workers actually hand tuberculosis patients their medications every morning and watch them swallow has been credited with substantially increasing cure rates for the disease in the last five years.

Other new gadgets encourage patients to supervise themselves. A famous prototype for these devices was the circular container developed in the 1960's to help women remember their daily oral contraceptive pill. Flat blister-packs of prescription medications are now widely used in Europe to serve the same purpose, Dr. Urquhart said.

At the AIDS clinic at Yale-New Haven Hospital, every patient is supplied with a large rectangular pillbox whose 28 compartments can hold a week's worth of medications to be taken several times a day, said Dr. Gerald Friedland, a professor of medicine at Yale who directs the AIDS program. Current treatment for AIDS requires patients to take up to two dozen pills daily, often with different requirements for each, like an empty or a full stomach. 'What's special about H.I.V. infection is the sheer complexity of the medications,' Dr. Friedland said. 'One of the definite predictors of poor adherence to treatment is the complexity of the regimen.'

Other gadgets now on the market include simple electronic alarms that can be programmed to sound at intervals throughout the day, like the ALR tag made by TDI, and more sophisticated beepers that flash messages ('Time to take a gemfibrozil now,' one made by Medprompt might tell patients with heart disease) as well.

And the newest devices entering offices and clinics can actually provide patients with little monthly medication report-cards, for both patient and doctor to inspect and try to improve.

They are pill-bottle caps fitted with a battery and a computer chip that remembers every time the bottle cap is opened and closed. Once a month the chip's memory can be downloaded into a computer and turned into a graph of exactly when during the month the patient dipped into the vial." (see New York Times, Science Times, Jun. 2, 1998).

Hirsch et al. U.S. Pat. No. 5,084,482 discloses a novel method employing compositions containing as an active antioxidant or anti-inflammatory agent the amino acid methionine, and/or one or more related compounds.

This disclosure is based on the discovery that certain methionine or methionine-type companies in the dl-form or d-form at relatively high well-tolerated doses are potent antioxidant and anti-inflammatory agents in man and animals. The methionine compounds in high daily dosage thus may act in vivo to inhibit oxidative effects. All the preferred methods include at least one methionine compound.

Stamler U.S. Pat. No. 5,385,937 discloses administration of a nitrosating compound, such as nitroglycerin, nitric oxide etc. and related compounds for the treatment or prevention of disease states resulting from hyperhomocystinemia.

Valentine et al. U.S. Pat. No. 5,427,799 discloses sustained release composition and method utilizing xanthan gum and an active ingredient such as niacin or analgesic. Xanthan gum and an excipient promotes sustained release.

Kuhits U.S. Pat. No. 5,466,469 discloses a Granular Drug Delivery System utilizing a gel-forming dietary fiber and pharmaceutically active compound.

Fike U.S. Pat. No. 5,612,382 discloses a composition for percutaneous absorption of pharmaceutically active ingredients aspirin, vitamins, vasodilators, and/or analgesics in hydroxyalkyl amide as carrier for transdermal treatment of certain ailments.

Lockett U.S. Pat. No. 5,626,884 discloses a maintenance regime with controlled intake of particular vitamins, mineral and micronutrient formulations, drastically reducing the incidence and severity of sickle cell disease crisis.

Ismail U.S. Pat. No. 5,656,620 discloses treatment and prophylaxis of pain involving administration of vitamin E combined with salicylic acid in a pharmaceutically acceptable carrier or adjuvant.

Moshyedi U.S. Pat. No. 5,770,215 discloses a vitamin supplement containing in one tablet from 5% to 1000% of the RDA of vitamins and a therapeutically effective amount of vascular occlusion inhibiting compound which is preferably aspirin. The vitamins are selected from vitamins A, D, E, K, C, thiamin, riboflavin, niacin, niacinamide, B6, folate, B12, biotin, pantothenic acid and mixtures thereof. Herbal and mineral ingredients can also be present. The composition can be in one capsule or one tablet form.

Against this background there remains a need for improved formulations which can be effectively produced and taken, and improved presentation thereof for facilitated compliance with prescribed medication including such formulations, for preventing and limiting coronary heart disease, strokes, heart attacks and peripheral vascular disease.

SUMMARY OF THE INVENTION

Definitions given below are used in the following disclosure of the invention and the claims.

ASA. Aspirin, i.e. all forms of acetylsalicylic acid including buffered aspirin, enteric coated aspirin, aspirin salts such as calcium acetylsalicylate, and mixtures of aspirin with acid acceptors. ASA does not include salicylic acid and its salts.

Vitamin B6. Pyridoxine hydrochloride in all physiologically acceptable forms.

Folic acid. Folate in all physiologically acceptable forms usually free folic acid.

Vitamin B12. Cyanocobalamin in all physiologically acceptable forms.

The term "consisting essentially of" is used in its art-recognized meaning to indicate that the composition is open to the inclusion of only such additional ingredients as do not adversely affect the advantageous properties of the composition.

In accordance with this invention, the incidence and severity of CAD, stroke, primary and subsequent heart attacks and PVD in humans is reduced by daily administration of an effective amount of a combination consisting essentially of ASA acetylsalicylic acid, a cyanocobalamin compound (Vitamin B12), a folic acid compound, and a pyridoxine compound (Vitamin B6).

As a result of unexpectedly favorable interaction of these ingredients in certain proportions, the amounts of each required for effectiveness are modest, thus enabling avoidance of side effects and facilitating compliance with a prescribed regimen.

Also in accordance with this invention, compliance with instruction or recommendation or prescription to take the combination of this invention is facilitated by the provision of a single package combination (henceforth referred to as a "daily administration pack") including the quantities of ASA acetylsalicylic acid, a cyanocobalamin compound (Vitamin B12), a folic acid compound, and a pyridoxine compound (Vitamin B6) to be administered once daily. The daily administration pack is stable in storage over long periods of time, so that a number of such daily administration pack combinations can be assembled in an over-pack to provide treatment for a month or longer as instructed or recommended by the practitioner. Moreover, multiple over-packs can be supplied and warehoused commercially.

Within the daily administration pack combination, the desired quantities of cyanocobalamin compound (Vitamin B12), a folic acid compound, and a pyridoxine compound (Vitamin B6) can be presented in a single dosage form or in a plurality of dosage form, such as one, two or three tablets, as found convenient, while ASA is kept separate in order to maximize storage stability. One way for ASA to be kept separate is simply to include an ASA tablet in the pack along with the one or several dosage forms used to present the vitamin ingredients. In addition, the daily administration pack can be partitioned on the inside Lo provide a compartment for an ASA tablet and one or more compartments for vitamins, or can have a "blister" containing an ASA tablet connected to the outside. As a result, a further advantage of the daily administration pack of the invention is that the ASA ingredient can be taken ahead of the remaining ingredients, at the same time, or some time after the other ingredients for additional flexibility in administration.

Also in accordance with this invention, atherogenic risk, heart attack and stroke can be diminished in a significant portion of the population, male and female, and as a result the need for hospitalizations, extensive recuperative therapy or expensive blood analysis and monitoring with associated cumulative and rising health care costs are diminished and in many cases eliminated.

In a human subject, daily administration of the daily administration pack combination of the invention over a period of several days provides a decrease in serum levels of homocystine, decreased coagulability, decreased serum levels of intermediate density lipoprotein (IDL) and dense low density lipoprotein (LDL), and decreased oxidative damage. Thus lifelong therapy is prudent. Daily administration of the daily administration pack combination of the invention can provide a number of therapeutic benefits to the recipient in improving all conditions that benefit in reduction in platelet agglutination and elevated homocystine level including the prevention of primary heart attack and stroke, and the prevention of any subsequent heart attack after a primary heart attack or stroke has occurred, restenosis after surgery and some peripheral vascular diseases.

DESCRIPTION OF PREFERRED EMBODIMENTS

Figure 1:
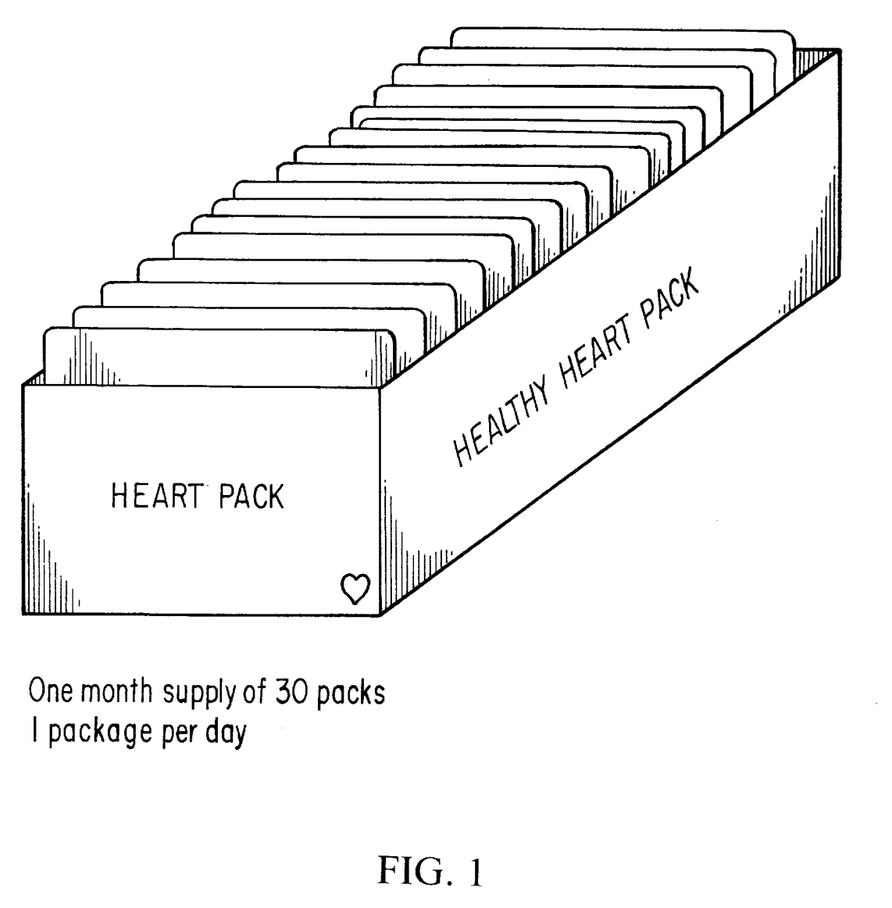
FIG. 1 is a partial view of a rectangular box holding a one-month supply of thirty daily administration packs according to this invention, of which twelve such packs are shown. A conventional cover for such a box is not shown.
Figure 2:
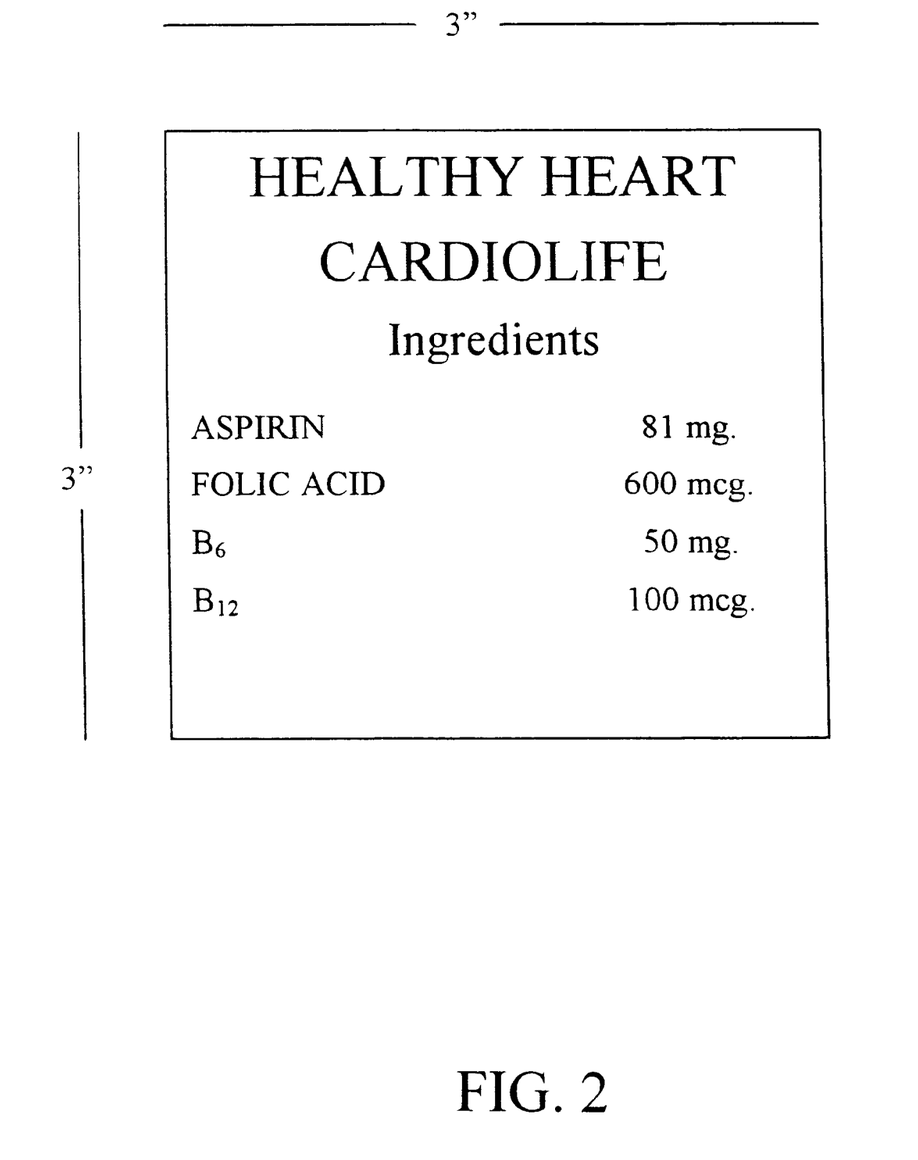
FIG. 2 and FIG. 3 each show a label printed on one side of or affixed to a daily administration pack according to this invention as illustrated in FIG. 1.
Figure 3:
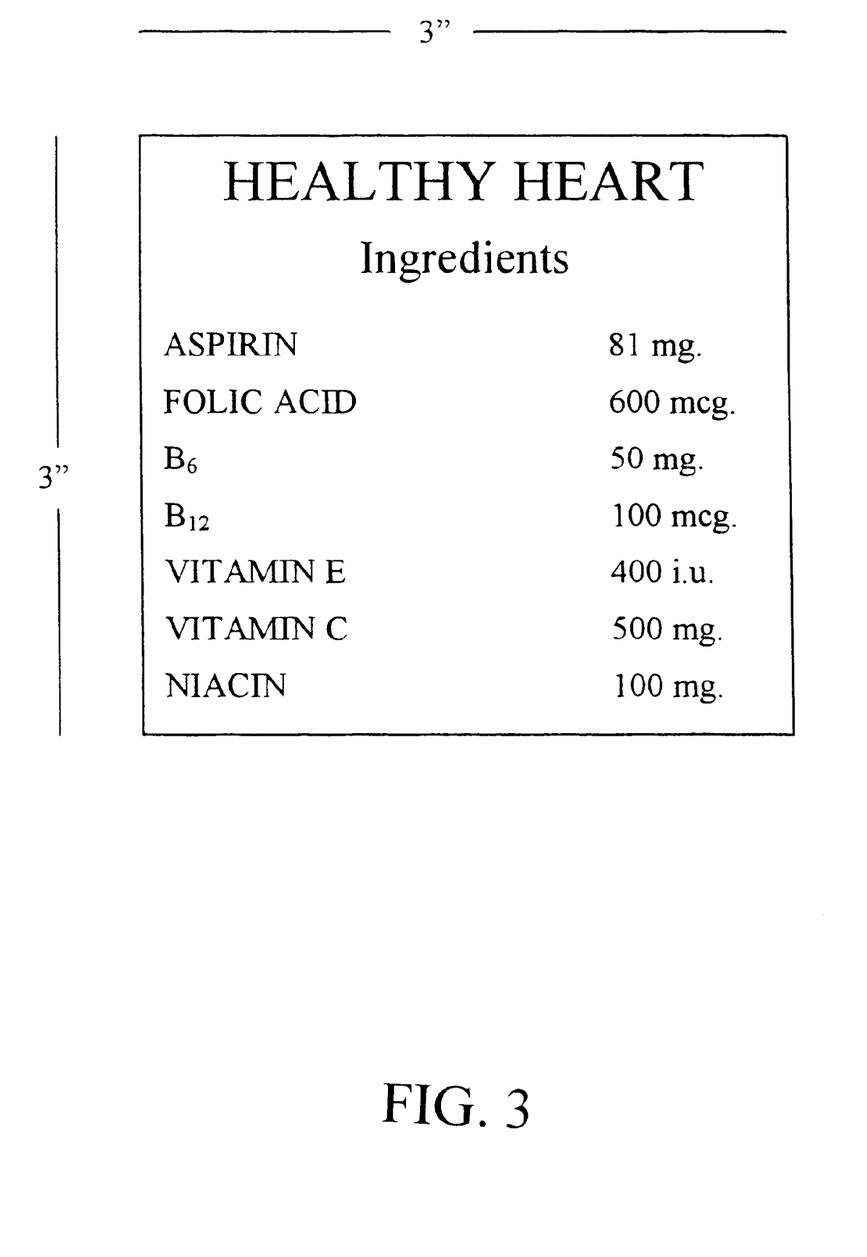
Figure 4:
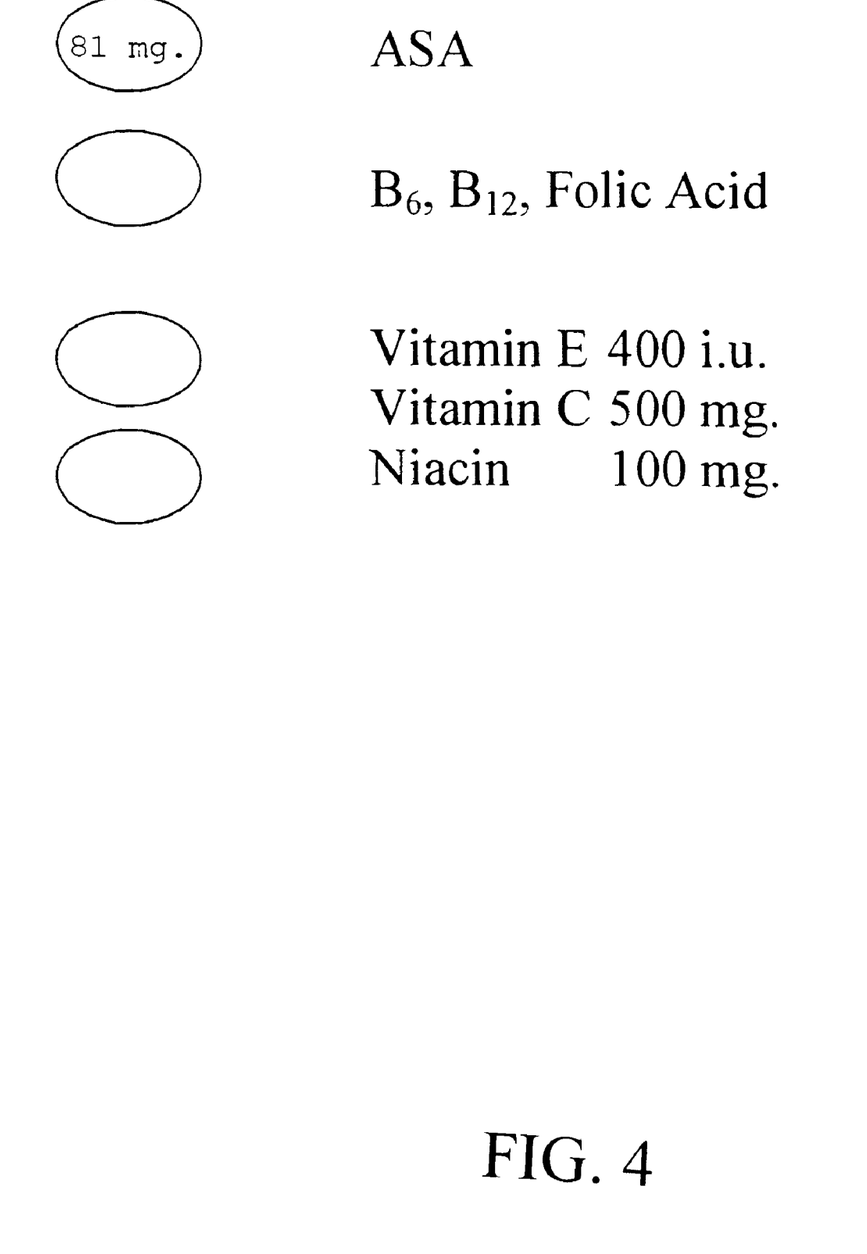
FIG. 4 is a visual diagram of four, distinctly separate tablets: one tablet containing aspirin 81 milligrams; the second tablet containing B-6, B-12 and folic acid; the third tablet containing vitamin E 400 i.u. and/or vitamin C 500 milligrams; and the fourth tablet containing niacin 100 milligrams. The third and fourth tablets in FIG. 4 could be any combination of vitamin E, vitamin C, or niacin.
Figure 5:
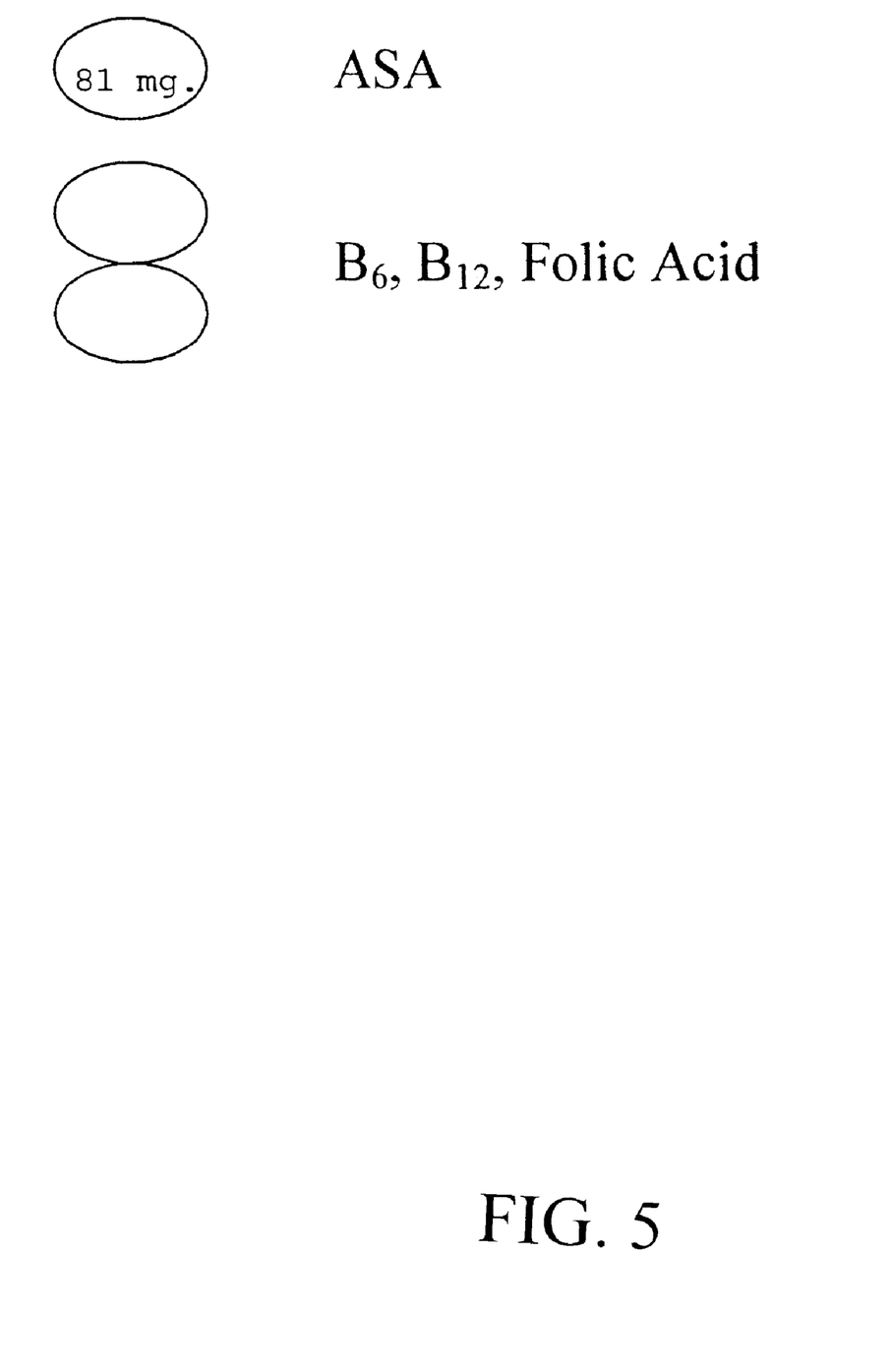
FIG. 5 shows three tablets: the first tablet containing aspirin 81 milligrams; the second and third tablet are any combination of B-6 and B-12 and folic acid.
Figure 6:
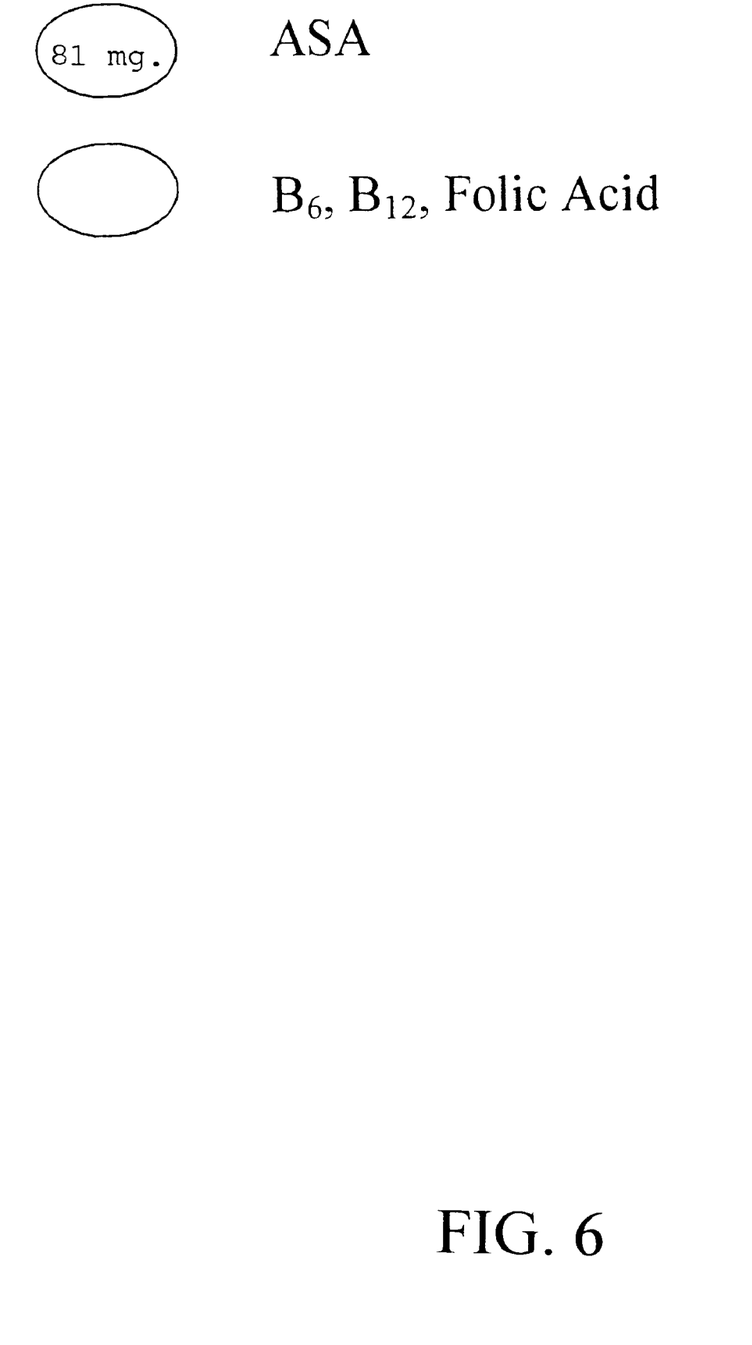
FIG. 6 shows two tablets: one containing aspirin and the second containing B-6 and B-12 and folic acid.

The daily administration pack according to this invention can be a pouch, plastic wrap, envelope, bottle, flask, or other container holding a supply of composition according to the invention.

The material of such pack can be any material that protects the contents and is not affected by the contents, such as cellophane, glass, metal, paper, and plastic, petroleum based, synthetic or wood products.

The composition to be contained in the daily administration pack can be presented in the form of powder, liquid, or shaped unit dosage forms such as tablets, capsules, and caplets in suitable packaging within a box or other suitable container.

In a particularly preferred embodiment, the daily administration pack can be a pouch made up of two sheets of aluminum foil or cellophane approximately 3 by 3 inches, heat sealed together after inserting the composition to be administered daily in the form of two or more tablets, of which one is an ASA tablet. The amount of ASA acetylsalicylic acid can range from 41 mg to 500 mg, preferably 50 to 200 mg. 81 mg is particularly preferred.

Vitamin B6 improves abnormal responses to methionine loading, especially in combination with folic acid. The dosage can range from 25 mg to 800 mg, preferably from 50 to 200 mg.

Folic acid at 650 micrograms per day lowered homocysteine levels by about 50% in subjects with initially elevated levels, about as good an effect as seen with higher doses. However, the dosage can range from 300 micrograms/day to 1400 micrograms/day. At folate intake higher than 1000 micrograms/day, there is concern that the hematologic manifestation of unrecognized vitamin B12 deficiency will be masked. Hence the need to prevent the possibility of masking a B12 deficiency by providing Vitamin B12 in adequate quantities of 25 to 800 microgram/day, preferably 100 to 300 microgram/day.

It is a feature of this invention that preferred levels of ASA in the daily administration pack include quantities well below the 325 mg of a standard adult ASA tablet while preferred levels of vitamins include quantities well above the nutritionally recommended daily allowances (RDA).

Certain optional ingredients can be included in the daily administration pack combination of the invention without adversely affecting its advantageous properties. Such ingredients include conventional tabletting excipients, edible coatings, and colorants. Also included if desired are Vitamin C and Vitamin E in effective antioxidant amounts, and niacin.

Vitamin C antioxidant is ascorbic acid in all physiologically acceptable forms including any one or more of the free acid, buffered ascorbic acid, calcium ascorbate, magnesium ascorbate, fat soluble esters such as ascorbyl palmitate, and associated bioflavanoids such as citrus bioflavanoids, hesperidin, quercetin, and rutin.

Vitamin E antioxidant is alpha-tocopherol in all physiologically acceptable forms including natural d-alpha-ocopherol with mixed tocopherols including beta-, delta-, and gamma-tocopherol and Vitamin E dl alpha tocopheryl acetate.

Niacin is nicotinic acid or pyridine-3-carboxylic acid as the free acid, its salts, and its amide also known as niacinamide.

Niacin and niacinamide when present can range from 100 mg to 3000 mg, preferably 300 to 700 mg/day depending on the tolerance of the patient, whether the niacin is time-release or slow-release and whether possible flushing is prevented by the prior use of ASA.

Vitamin E antioxidant when present can range from 100 to 800 IU, preferably 300 to 500 IU per day. Vitamin E can be as an oil, powder, or in liquid form.

Vitamin C antioxidant when present can range from 400 mg to 2000 mg, preferably 500 to 1500 mg per day, and can be in the form of powder, liquid, or crystal.

EXAMPLE 1

PREPARATION OF DAILY ADMINISTRATION PACK

Tablets were prepared containing the following amounts of active ingredients according to this invention.

ASA 81 milligrams
B6 50 milligrams
B12 100 micrograms
Folic acid 600 micrograms
together with excipient and colorant inert ingredients.

A sealed pack for daily administration contained one ASA tablet and one or more tablets including B6, B12, and folic acid as described.

EXAMPLE 2

PREPARATION OF DAILY ADMINISTRATION PACK WITH OPTIONAL ADDITIVES

Tablets were prepared containing the amounts of active ingredients according to this invention and optional additives as shown.

ASA 81 milligrams
B6 50 milligrams
B12 100 micrograms
Folic acid 600 micrograms
Vitamin C antioxidant 500 milligrams
Vitamin E antioxidant 400 International Units (IU)
Niacin 500 milligrams A sealed pack for daily administration contained one ASA tablet and a second tablet including amounts of B6, B12, folic acid, Vitamin C, Vitamin E, and niacin as described, together with excipient and color.

EXAMPLE 3

PREPARATION OF DAILY ADMINISTRATION PACK CONTAINING MULTIPLE TABLETS

Daily administration packs were prepared containing a separate tablet for each active ingredient according to this invention in the amounts stated below:

ASA 81 milligrams
B6 50 milligrams
B12 100 micrograms
Folic acid 900 micrograms
together with excipient and colorant inert ingredients.

EXAMPLE 4

PREPARATION OF DAILY ADMINISTRATION PACK CONTAINING MULTIPLE TABLETS INCLUDING OPTIONAL ADDITIVES

Daily administration packs were prepared containing a separate tablet for each of the following ingredients in the amounts stated below:
ASA 81 milligrams
B6 50 milligrams
B12 100 micrograms
Vitamin C antioxidant 500 milligrams
Vitamin E antioxidant 400 International Units (IU)
Folic acid 600 micrograms
Niacin 500 milligrams
together with excipient and colorant inert ingredients.

EXAMPLE 5

IMPROVED COMPLIANCE

A 52 year old white male with a family history of heart disease and stroke could not remember to take multiple pills from four bottles on a daily basis to lower the incidence and or severity of heart attack or stroke. This problem was avoided by the daily administration of one pack according to Example 4 and thus improved compliance 100%.

EXAMPLE 6

TREATMENT FOR REDUCED RISK OF HEART ATTACK AND STROKE

A 65 year old white female with a family history of stroke and heart attack is treated with a daily administration pack according to Example 1 for a lowered incidence and decreased severity for stroke and heart attack.

EXAMPLE 7

TREATMENT FOR REDUCED RISK OF THE INCIDENCE OF RESTENOSIS

A 74 year old white male with a history of stenosis is placed on a daily administration pack according to Example 4 for lowered incidence of restenosis and attendant problems.

EXAMPLE 8

TREATMENT FOR REDUCTION OF HOMOCYSTINE LEVELS AND DECREASED INCIDENCE OF HEART ATTACK AND STROKE

A 49 year old white male with a history of elevated homocysteine and increased risk of heart attack is given a daily administration pack according to Example 1 for a decreased incidence of heart attack, stroke and a lowered level of homocysteine.

EXAMPLE 9

IMPROVED COMPLIANCE FOR REDUCED RISK OF HEART ATTACK AND STROKE

A 56 year old black male with a history of heart disease, stroke and elevated homocysteine in the family who has not complied with medical instructions in finding and opening multiple bottles of vitamins, supplements and aspirin and finding the right ingredients is now in compliance with his doctor's instructions by taking once a day a daily administration pack according to example 4 which contains all the necessary ingredients.

EXAMPLE 10

TREATMENT FOR REDUCED RISK OF HEART ATTACK AND STROKE

A 42 year old white male with a family history of heart attack takes the instructed daily administration pack according to Example 1 and significantly reduces the chance of a stroke or heart attack.

The foregoing description is intended as illustrative and is not to be taken as limiting. Still other variations within the spirit and scope of this invention as defined by the claims are possible and will readily present themselves to those skilled in the art.

What is claimed is:

1. The method of reducing the incidence and severity of primary heart attack, stroke and any subsequent heart attack or stroke in humans by daily administration of an effective amount of a combination of acetylsalicylic acid (ASA), a cyanocobalamin compound (Vitamin B12), a folic acid compound, and a pyridoxine compound (Vitamin B6).

2. The method of claim 1 in which ASA is any one or more of free acetylsalicylic acid, buffered aspirin, or enteric coated aspirin in a unit dose of 41 milligrams to 200 milligrams expressed as free aspirin.

3. The method of claim 1 in which ASA is enteric coated aspirin.

4. The method of claim 1 in which the Vitamin B12 compound is in a unit dose of 25 micrograms to 800 micrograms, the folic acid compound is free folic acid in a unit dose of 300 micrograms to 1400 micrograms expressed as free folic acid, and the Vitamin B6 compound is pyridoxine hydrochloride in a unit dose of 25 milligrams to 800 milligrams.

5. The method of claim 1 in which administration of the combination is by mouth.

6. A daily administration pack for reducing the incidence and severity of stroke, primary heart attack, and any subsequent heart attack or stroke in humans, consisting essentially of an effective amount of acetylsalicylic acid (ASA), an effective amount of a cyanocobalamin compound (Vitamin B12), an effective amount of a folic acid compound, and an effective amount of a pyridoxine compound (Vitamin B6).

7. A daily administration pack according to claim 6 in which Vitamin B6, Vitamin B12 and folic acid are combined in a single unit dosage form.

8. A daily administration pack according to claim 6 in which each of ASA, Vitamin B6, Vitamin B12, and folic acid are present in a separate unit dosage form.

9. A daily administration pack according to claim 6 in which the amount of ASA is 41 milligrams to 200 milligrams expressed as free aspirin, the amount of Vitamin B6 is 25 milligrams to 500 milligrams expressed as pyridoxine), the amount of Vitamin B12 is 25 micrograms to 800 micrograms expressed as cyanocobalamin, and the amount of folic acid is 300 micrograms to 1400 microgram expressed as free folic acid.

10. A daily administration pack according to claim 6 additionally including an effective amount of at least one substance selected from the group consisting of Vitamin C antioxidant, Vitamin E antioxidant, and niacin.

11. A daily administration pack according to claim 10 in which the amount of ASA is 41 milligrams to 200 milligrams expressed as free aspirin, the amount of antioxidant when present is 0 to 2000 milligrams expressed as free ascorbic acid and/or 0 to 800 International Units expressed as Vitamin E activity, the amount of Vitamin B6 is 25 milligrams to 500 milligrams expressed as pyridoxine), the amount of Vitamin B12 is 25 micrograms to 800 micrograms expressed as cyanocobalamin, the amount of folic acid is 300 micrograms to 1400 micrograms expressed as free folic acid, and the amount of niacin when present is 0 to 700 milligrams.

12. A composition according to claim 6 for reducing the incidence and severity of stroke, primary heart attack, and any subsequent heart attack in humans consisting essentially of the active ingredients ASA 81 milligrams B6 50 milligrams B12 100 micrograms Folic acid 600 micrograms together with 0 to 1000 milligrams of excipient and 0 to 1000 milligrams of colorant inert ingredients.

* * * * *